United States Patent [19]

Allen

[11] Patent Number: 6,133,405

[45] Date of Patent: Oct. 17, 2000

[54] POLYALKANOLAMIDE TACKIFYING RESINS FOR CREPING ADHESIVES

[75] Inventor: Anthony J. Allen, Wilmington, Del.

[73] Assignee: Hercules Incorporated, Wilmington, Del.

[21] Appl. No.: 08/891,199

[22] Filed: Jul. 10, 1997

[51] Int. Cl.[7] ............................ C08G 69/08; C08G 73/10; B31F 1/12; D21H 11/00
[52] U.S. Cl. .......................... 528/310; 528/170; 528/172; 528/173; 528/220; 528/229; 528/322; 528/327; 528/332; 528/335; 528/336; 528/345; 525/66; 162/111
[58] Field of Search ....................... 528/310, 170, 528/172, 173, 220, 229, 322, 327, 332, 335, 336, 345; 162/111; 525/66

[56] References Cited

U.S. PATENT DOCUMENTS

| | | | |
|---|---|---|---|
| 2,089,212 | 4/1937 | Kritchevsky | 260/124 |
| 2,096,749 | 10/1937 | Kritchevsky | 260/124 |
| 2,386,454 | 10/1945 | Frosch | 260/78 |
| 2,396,248 | 3/1946 | Christ | 260/78 |
| 2,464,094 | 3/1949 | Meade et al. | 260/404 |
| 2,844,609 | 7/1958 | Tesoro et al. | 260/404 |
| 2,863,888 | 10/1958 | Schurman | 260/404 |
| 3,556,932 | 1/1971 | Coscia et al. | 162/166 |
| 3,640,841 | 2/1972 | Winslow et al. | 162/164 |
| 4,075,177 | 2/1978 | Bonnet et al. | 260/75 |
| 4,501,640 | 2/1985 | Soerens | 162/111 |
| 4,528,316 | 7/1985 | Soerens | 524/503 |
| 4,684,439 | 8/1987 | Soerens | 162/111 |
| 4,788,243 | 11/1988 | Soerens | 524/503 |
| 4,994,146 | 2/1991 | Soerens | 162/112 |
| 5,043,152 | 8/1991 | Schaefer et al. | 424/5 |
| 5,179,150 | 1/1993 | Furman, Jr. et al. | 524/376 |
| 5,187,219 | 2/1993 | Furman | 524/377 |
| 5,240,630 | 8/1993 | Sabahi et al. | 252/68 |
| 5,338,807 | 8/1994 | Espy et al. | 525/430 |
| 5,494,554 | 2/1996 | Edwards et al. | 162/111 |
| 5,498,315 | 3/1996 | Dragner et al. | 162/164.6 |
| 5,554,634 | 9/1996 | Anderson et al. | 514/370 |
| 5,660,687 | 8/1997 | Allen et al. | 162/111 |

FOREIGN PATENT DOCUMENTS

| | | |
|---|---|---|
| 979579 | 12/1975 | Canada . |
| 739709A | 10/1996 | European Pat. Off. . |
| 61-111328 | 5/1986 | Japan . |
| 4108196 | 4/1992 | Japan . |
| WO 96/25388 | 8/1996 | WIPO . |

OTHER PUBLICATIONS

Kirk–Othmer Encyclopedia of Chemical Technology, 3rd Ed., vol. 1, pp. 509 & 510 The date of publication is not available.

Kirk–Othmer Encyclopedia of Chemical Technology, 3rd Ed., vol. 13, pp. 347 & 348 The date of publication is not available.

D. W. Aubrey & M. Sherriff, J. Poly Sci.: Poly Chem. Ed., 16, pp. 2631–2643 (1978) The month of publication is not available.

*Primary Examiner*—P. Hampton-Hightower
*Attorney, Agent, or Firm*—Martin F Sloan; Ivan G Szanto

[57] ABSTRACT

Water soluble polyalkanolamides and a process to prepare same by reacting polycarboxylic acid or its anhydride, ester or halide derivative with at least one alkanolamine and optionally with a polyamine and removing the condensation byproduct water, alcohol or hydrogen halide.

41 Claims, 10 Drawing Sheets

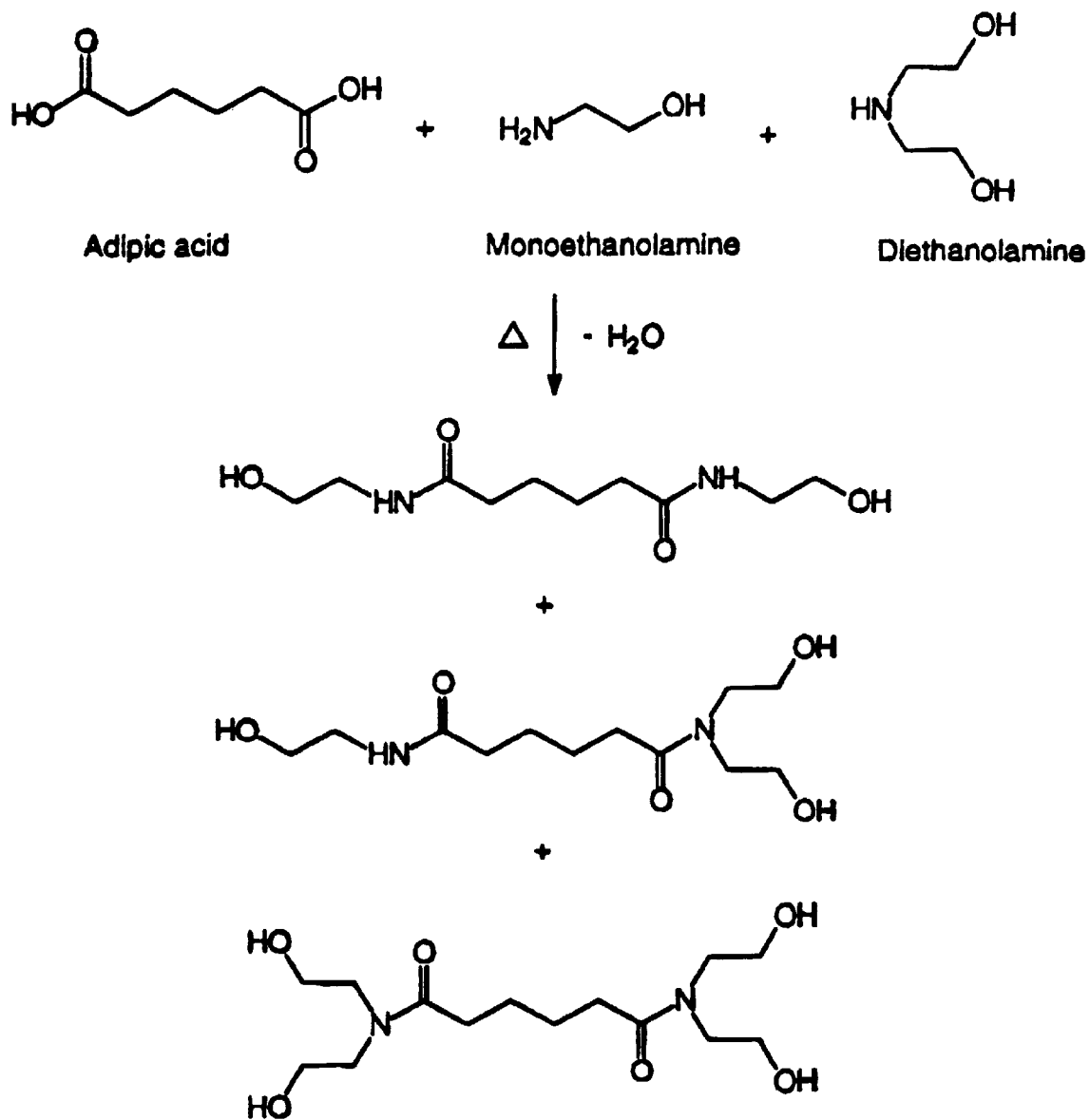
Figure 1. Synthesis of Polyalkanolamide

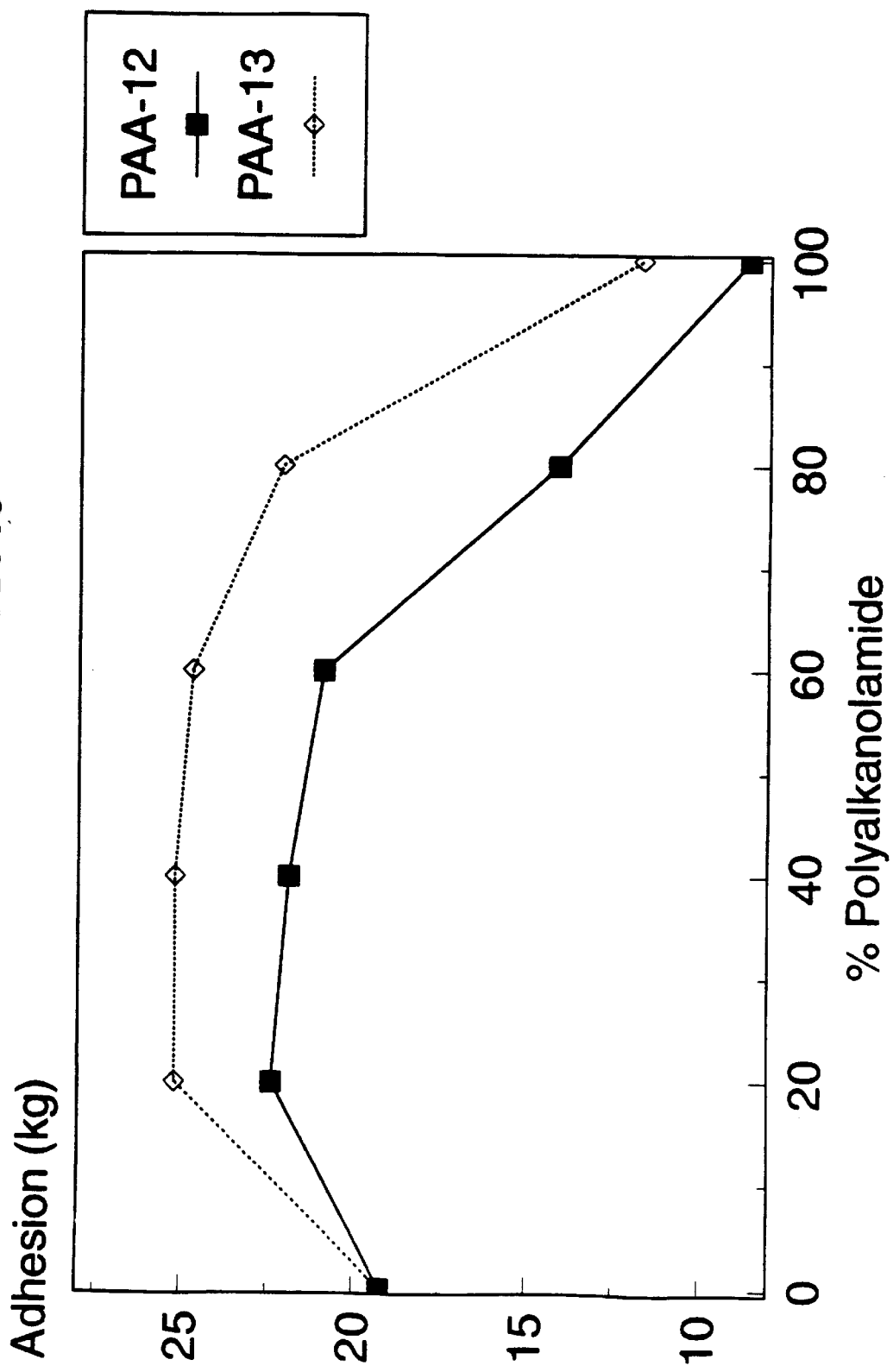
Figure 2. Testing Crepetrol 80E with PAA 12 and PAA 13

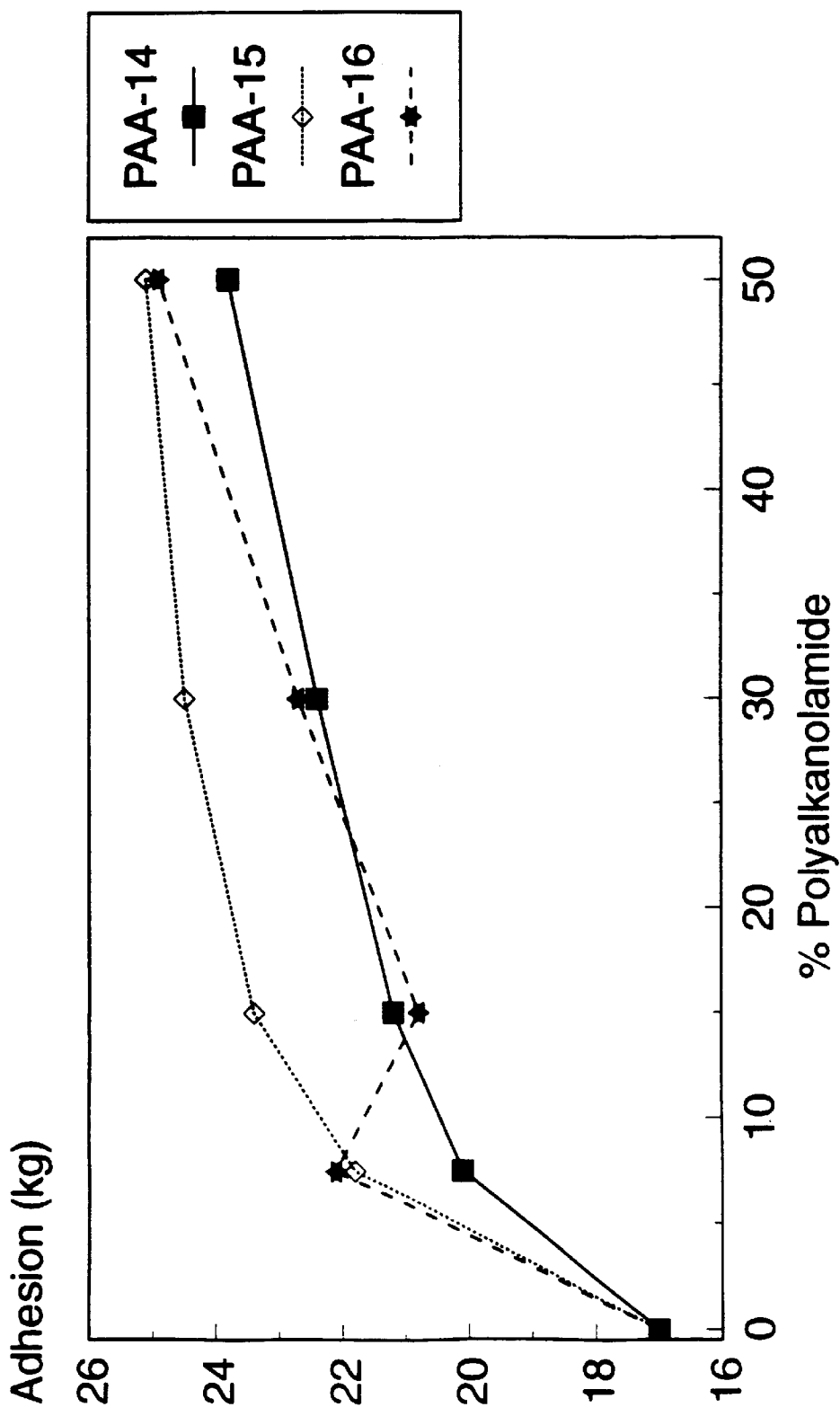

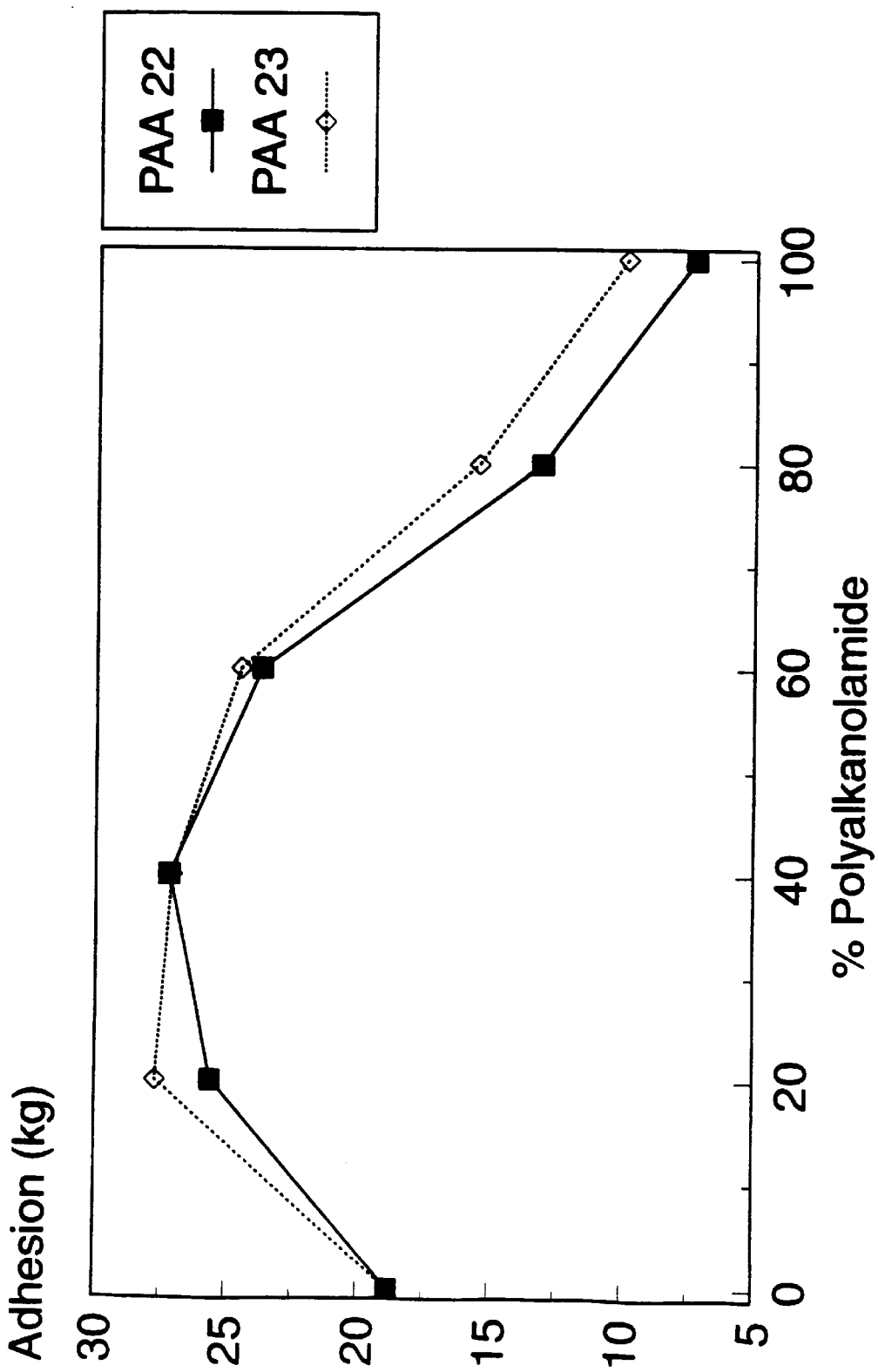
Figure 4. Testing Crepetrol 80E with PAA 22 and PAA 23

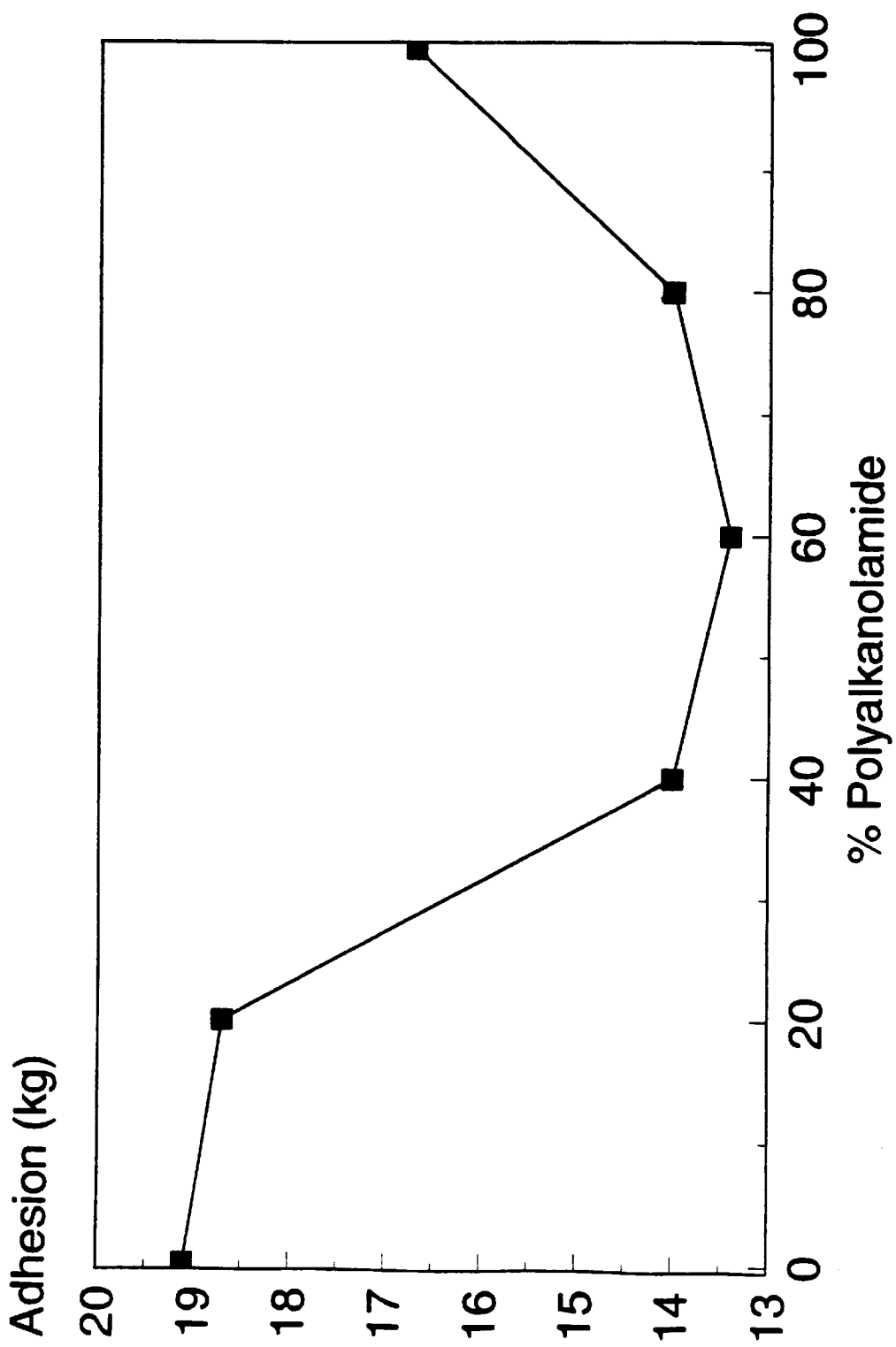

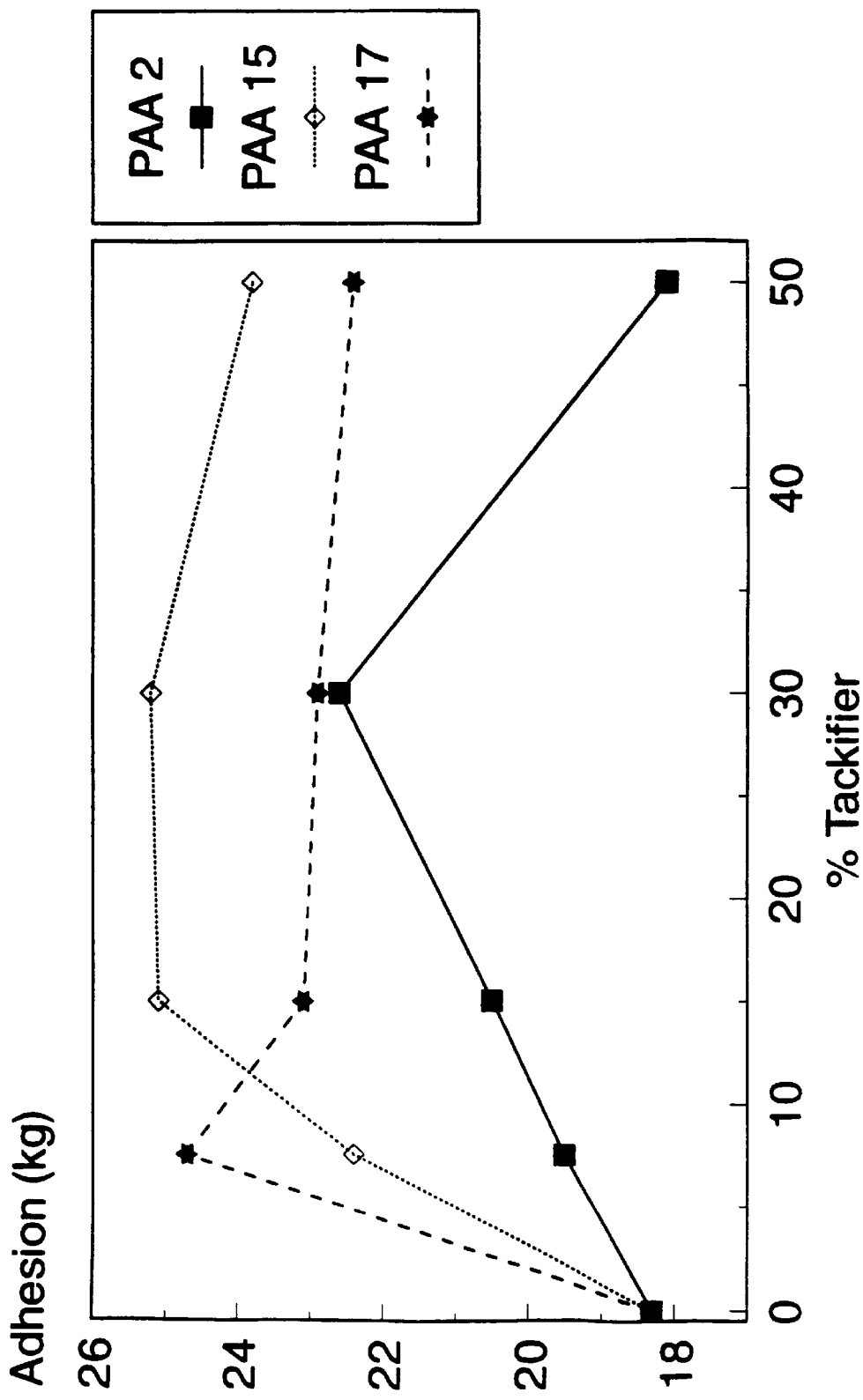
Figure 6. Testing of Kymene 557LX with PAA 2, PAA 15 and PAA 17

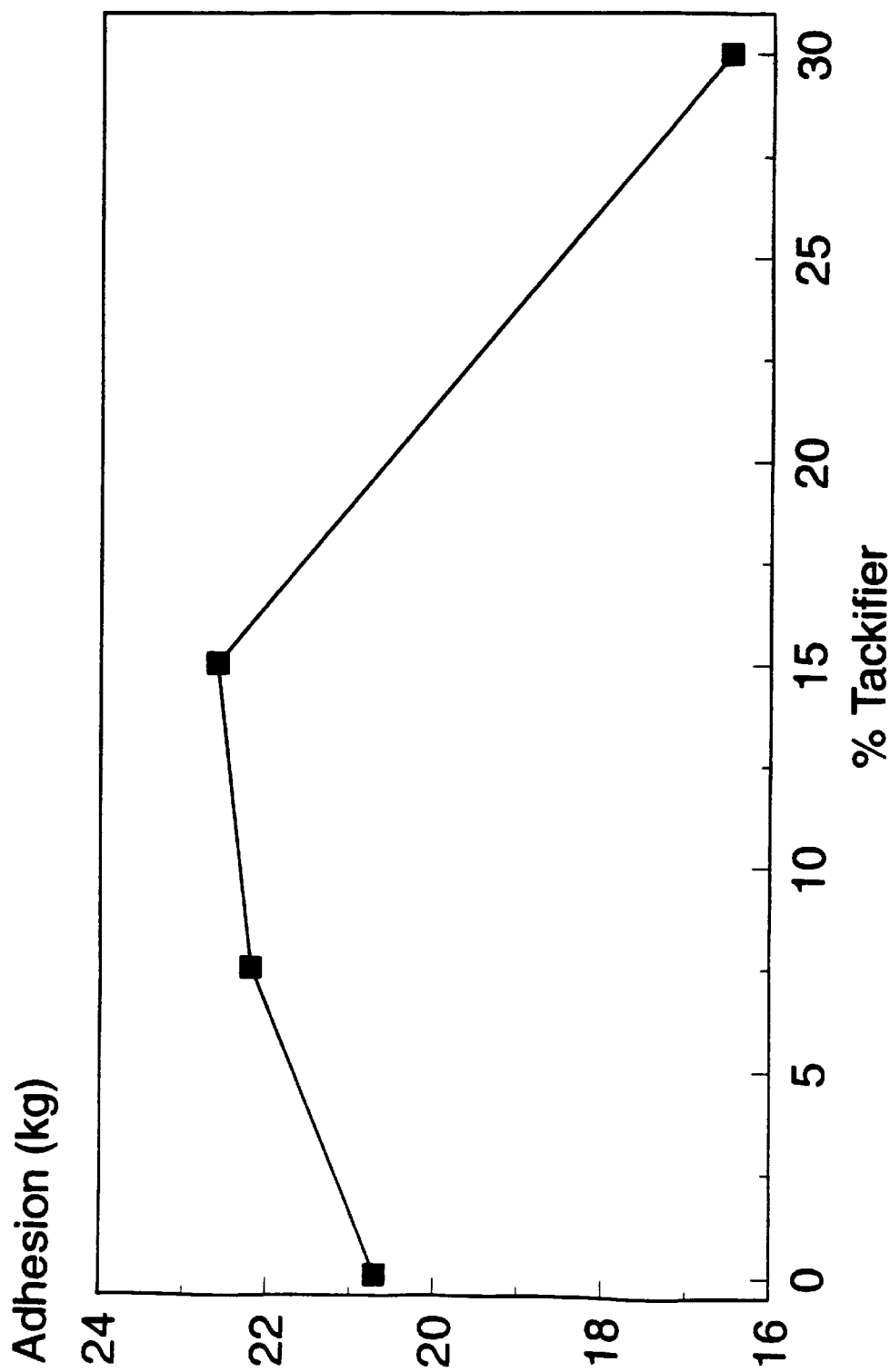
Figure 7. Testing of Crepetrol 73 with PAA 2

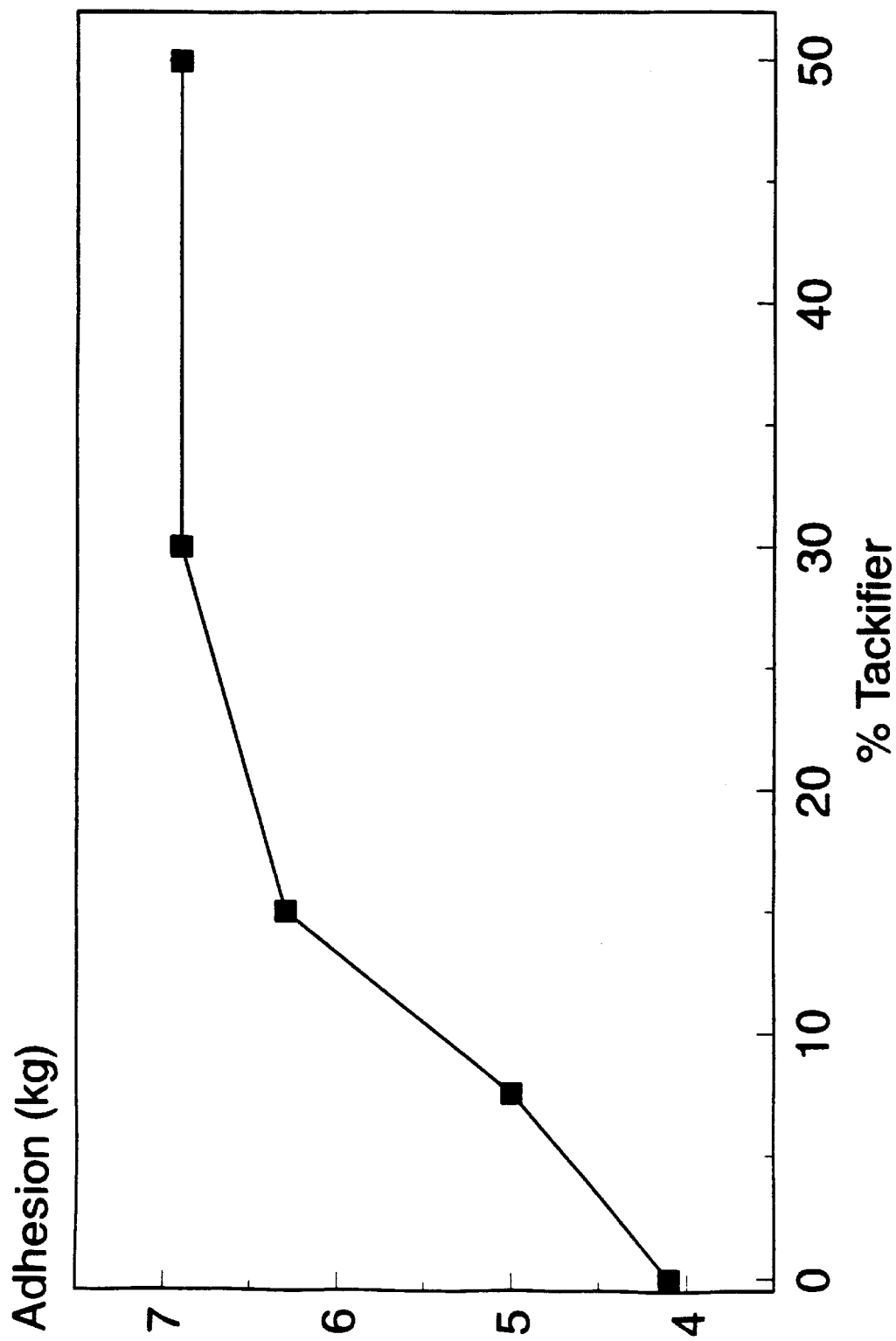

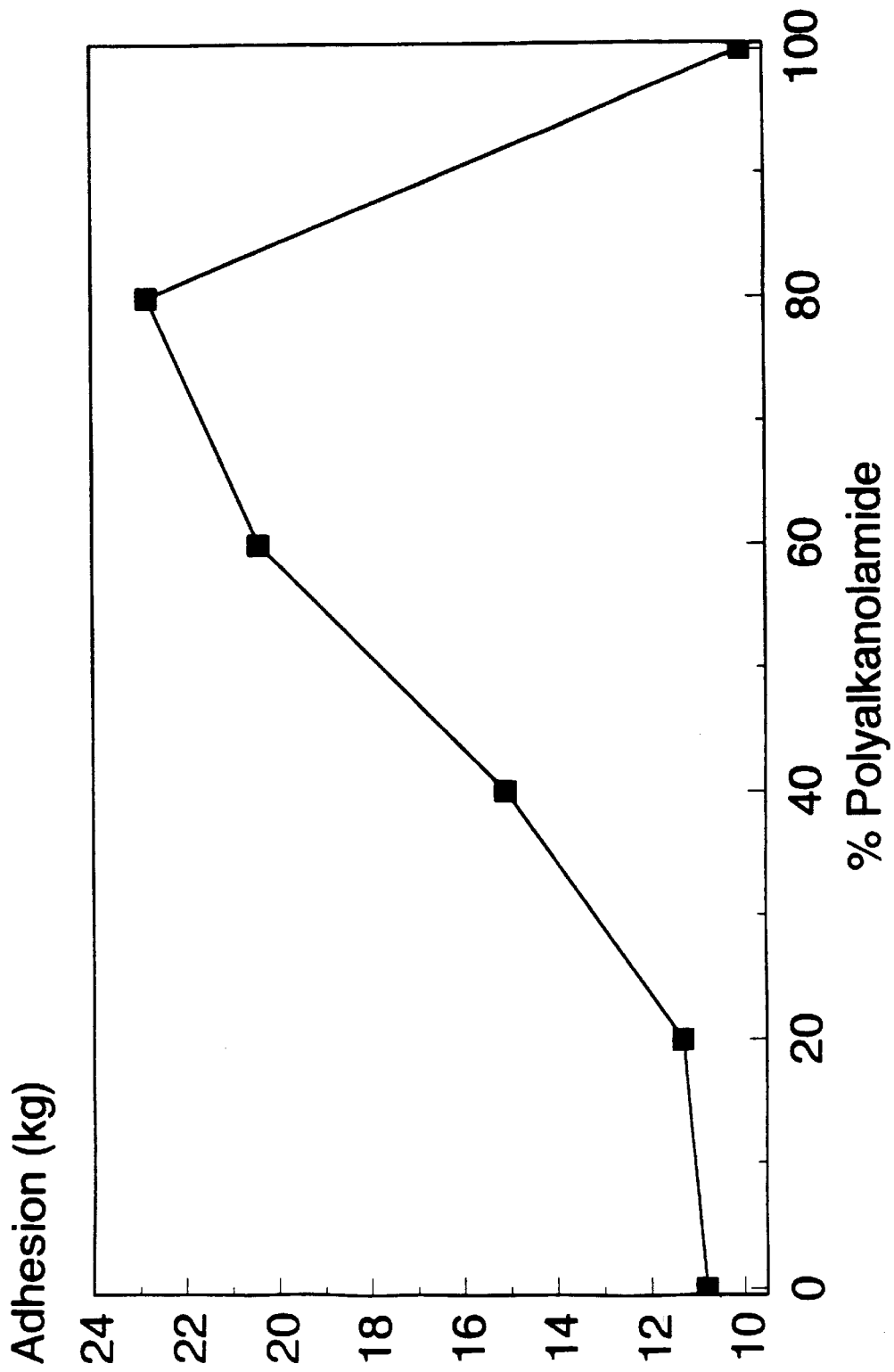

Figure 10. Synthesis of Polyalkanolamide Containing an Oligomeric Polyamide Group
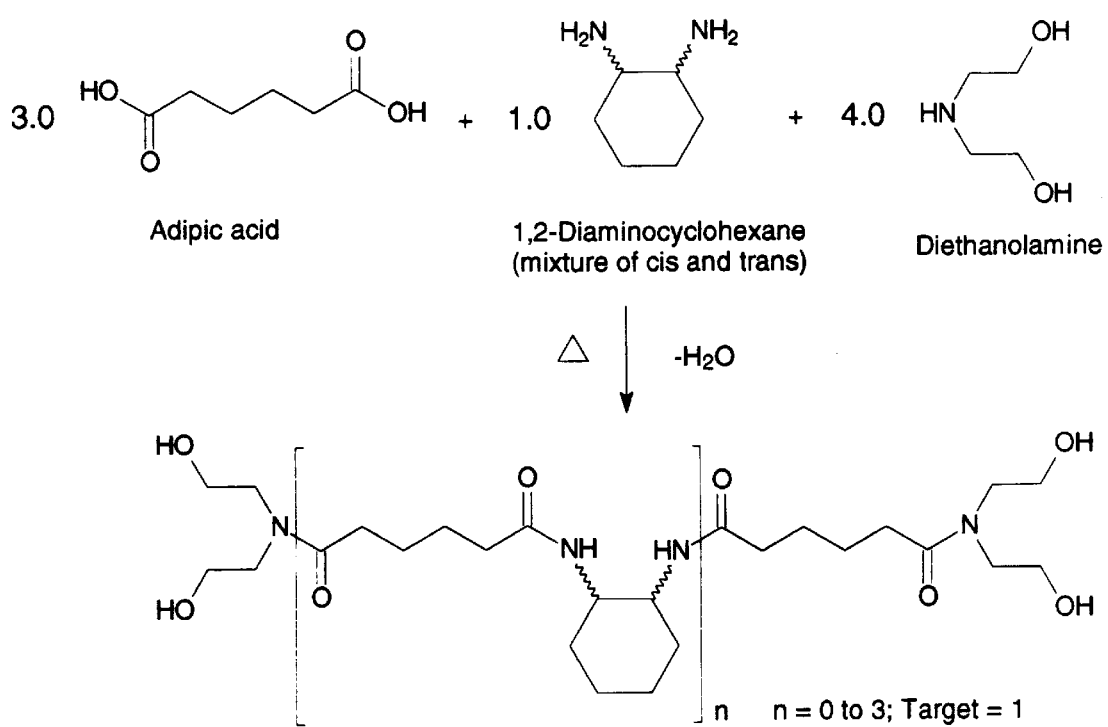

POLYALKANOLAMIDE TACKIFYING RESINS FOR CREPING ADHESIVES

BACKGROUND OF THE INVENTION

1. Field of the Invention

The present invention relates to new creping adhesives and more particularly it relates to polyakanolamide tackifiers obtained from the condensation of polycarboxylic acids with alkanolamines.

2. Description of the Prior Art

Alkanolamides prepared from the reaction of alkanolamines with monofunctional long chain fatty acids have been described in the patent literature. The earliest example is of the alkanolamide obtained from a 2:1 molar mixture of alkanolamine and fatty acid described in 1937 by W. Kritchevsky in U.S. Pat. Nos. 2,089,212 and 2,096,749. These are low purity, water-soluble products that contain high levels of unreacted alkanolamine. The water solubility is a direct result of the presence of the large amounts of unreacted alkanolamine. This type of material has found utility as a component of surfactant formulations.

Another type of alkanolamide composition has been described in the patent literature that is prepared by reacting equimolar amounts of a fatty acid ester with an alkanolamine to yield a higher purity alkanolamide. E. M. Meade, U.S. Pat. No. 464,094; G. C. Tesoro, U.S. Pat. No. 2,844,609; J. V. Schurman, U.S. Pat. No. 863,888. These compounds are not water soluble by themselves. They can be rendered soluble in water by combining them with an anionic or nonionic surfactant. These alkanolamides are also useful in surfactant formulations.

A number of water-soluble adhesive compositions used in the creping process have been described in the patent literature. Canadian patent No. 979,579, U.S. Pat. No. 5,338,807, U.S. Pat. No. 4,075,177, U.S. Pat. No. 3,640,841 and U.S. application Ser. No. 08/1428,287, filed Apr. 25, 1995, all describe water-soluble polyamidoamine-based compositions that function as adhesives for the creping process in papermaking. Other patents such as U.S. Pat. No. 4,501,640, U.S. Pat. No. 4,584,439, U.S. Pat. No. 4,788,243, U.S. Pat. No. 4,528,316 and U.S. Pat. No. 5,179,150 describe mixtures of poly(vinyl alcohol) and polyamide polymers that are useful as creping adhesives.

Tackifying resins are an essential component of rubber-based adhesives. "Kirk-Othmer Encyclopedia of Chemical Technology", 3rd Ed., Vol 1, pp. 509 & 510 and Kirk-Othmer Encyclopedia of Chemical Technology", 3rd Ed. Vol. 13, pp. 347 & 348. These tackifiers are hydrocarbon materials based on rosin esters, terpene resins (poly α- and β-pinene), petroleum-derived resins made from $C_5$ and $C_9$ feedstocks, coumarone-indene resins and copolymers of α-methylstyrene and vinyltoluene. These are hydrocarbon-based, hydrocarbon-soluble materials that are typically used with hydrocarbon-based, hydrocarbon-soluble rubbers such as natural rubber and styrene-butadiene rubber (SBR). The tackifying resins function by modifying the viscoelastic properties of the rubber adhesive that they are blended with. D. W. Aubrey & M. Sherriff, J. Poly Sci.: Poly Chem. Ed., 16, pp. 2631–2643 (1978).

U.S. Pat. No. 2,396,248 discloses a process for making polymers comprising heating at a temperature below 180° C. a reaction mixture comprising essentially bifunctional reactants comprising monoaminomonohydric alcohol and a dibasic carboxylic acid, heating the low molecular weight polymer at polymerizing temperatures until a polymer is formed which can be formed into pliable filaments, the carboxylic groups in the mixture of bifunctional reactants being present in an amount substantially equimolecularly equivalent to the sum of the amino and alcoholic hydroxyl groups. The polymers produced by this process are disclosed to have great strength, toughness, flexibility and elasticity and good fiber forming and cold drawing properties.

U.S. Pat. No. 2,386,454 discloses a microcrystalline linear polymer having permanent molecular orientation produced by the application of directional stress to the reaction product produced by condensing by heating a mixture including a monoalkylolamine which has at least one hydrogen atom attached to the hydrogen atom and an aliphatic carboxylic acid which has at least three carbon atoms between the carboxyl groups, under polymerizing conditions until substantially completely reacted, the carboxyl groups in the mixture being present in an amount substantially equimolecularly equivalent to the sum of the amino and alcoholic hydroxyl groups, and which reaction product is capable of being cold drawn into fibers exhibiting molecular orientation along the fiber axis. The polymers so obtained are disclosed to be suitable for coating, impregnating or fiber-forming purposes having high strength and elasticity.

SUMMARY OF THE INVENTION

According to the present invention there is provided a water-soluble polyalkanolamide having the formula:

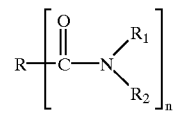

wherein n is an integer from 2 to 10,

R is selected from the group consisting of linear aliphatic or branched aliphatic or cycloaliphatic alkyl groups, alkylaryl groups and aryl groups, including those containing hetero atoms; heterocyclic groups; and oligomeric polyamide groups having a degree of polymerization ($DP_n$) of from about 1 to 6;

$R_1$ is selected from the group consisting of linear aliphatic or branched aliphatic or cycloaliphatic alkyl groups and having at least two C atoms and one alcohol functionality, including those containing heteroatoms;

$R_2$ is selected from the group consisting of H, linear aliphatic or branched aliphatic or cycloaliphatic alkyl groups, and linear aliphatic or branched aliphatic or cycloaliphatic alkyl groups having at least one alcohol functionality, including those containing heteroatoms.

According to the present invention there is also provided a process to prepare water-soluble polyalkanolamides comprising reacting polycarboxylic acid or its anhydride, ester or halide derivative, with at least one alkanolamine and optionally with a polyamine and removing the condensation byproduct water, alcohol or hydrogen halide.

Further according to the present invention there are provided processes for creping fibrous webs comprising applying the composition of the present invention to a drying surface for the fibrous web, pressing the fibrous web against the drying surface to adhere the web to the drying surface and dislodging the web from the drying surface with a creping device to crepe the fibrous web.

According to the present invention there is also provided creped paper made by applying the composition of the present invention to a drying surface, pressing the fibrous web against the drying surface and dislodging the web from the drying surface with a creping device.

BRIEF DESCRIPTION OF THE FIGURES

FIG. 1 is an illustration of the reaction for the synthesis of polyalkanolamides.

FIGS. 2 to 9 are illustrations of the effect of the polyalkanolamides of various Examples on the adhesion of various creping aids.

FIG. 10 is an illustration of the reaction for the synthesis of polyalkanolamides containing an oligomeric polyamide group.

DETAILED DESCRIPTION OF THE INVENTION

It has surprisingly been discovered that water-soluble polyalkanolamides prepared by the reaction of a polycarboxylic acid with an alkanolamine and optionally with a polyamine are good creping adhesives.

The compositions of the present invention are unique in that they contain at least two alkanolamide groups per molecule and are completely miscible in water. They do not contain hydrophobic(lipophilic) functional groups such as long alkyl chains, in contrast with the alkanolamide compositions made from fatty acids which are widely used in detergent formulations. The polyalkanolamides of the present invention are useful as creping adhesives and in modifying the adhesive properties of PAE resins and polyamine-epichlorohydrin resins as well as poly(vinyl alcohol).

These water-soluble polyalkanolamides also provide improvements in the adhesion of water-soluble polymers by a tackifying mechanism since they are highly condensed, low molecular weight materials that should have good miscibility and compatibility with water-soluble polymers. In particular, these materials have good compatibility with polyamidoamine-based polymers (e.g. polyamidoamine-epichlorohydrin resins), poly(vinyl alcohols), polyacrylamides, poly(2-hydroxyethyl (meth)acrylate), polyN-vinylpyrollidinone, hydroxyethyl cellulose (HEC), hydroxypropyl cellulose (HPC), starch, guar gum, agar and other water-soluble polysaccharides, due to the similar highly polar structural elements present in the polyalkanolamide tackifiers and these polymers (i.e. amide and alcohol functionalities), which render these materials water soluble. The polyalkanolamides are also effective in modifying the viscoelastic and adhesive properties of other water-soluble polymers such as poly(meth)acrylic acid poly(ethylene oxide), poly (ethylene glycol), polyethyleneimine (PEI), polyamine-epiclorohydrin resins, chitosan, alginic acid, and carboxymethyl cellulose (CMC).

The polyalkanolamides of the present invention are differentiated from the prior art in that they consist of a unique chemical composition consisting of the condensation product of a polycarboxylic acid and an alkanolamine, with or without an added polyamine, in proportions such that the total molar quantity of carboxylic acid groups and the total molar quantity of amine groups are essentially equal.

The reaction for preparing these materials is illustrated in FIG. 1, which shows the reaction scheme for the reaction of adipic acid with monoethanolamine (MEA) and diethanolamine (DEA). The starting materials are present in the reaction mixture with a ratio of carboxylic acid groups to alkanolamine of about 1.0:1.0. The polycarboxylic acid may be a single compound or a mixture of polycarboxylic acids and similarly the alkanolamine can be comprised of a single compound or a mixture of alkanolamine compounds. In addition, a low level of polyamine may be added to the reaction mixture in order to increase the molecular weight. The present invention is directed towards relatively low molecular weight compounds. The relatively low molecular weights of these polyalkanolamides is reflected by the low measured reduced specific viscosity (RSV) of the products (<0.052 dL/g) and the relatively low viscosity of the 50% solids aqueous solutions (<110 cPs for most products). In order to ensure an amorphous structure (i.e. non-crystalline) it may be advantageous to use mixtures of polycarboxylic acids and/or alkanolamines in the synthesis of the alkanolamides. The structure of the higher molecular weight oligomers is also advantageous in avoiding crystallinity due to the heterogeneity of the molecular species produced, i.e. the distribution of products having different molecular weights. Avoiding or minimizing crystallinity in these materials improves their effectiveness as tackifiers.

The water-soluble polyalkanolamides of the present invention have the formula:

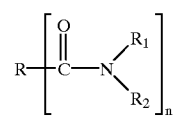

wherein n is an integer from 2 to 10, preferably from 2 to 6 and most preferably from 2 to 4, R is selected from the group consisting of linear aliphatic or branched aliphatic or cycloaliphatic alkyl groups, alkylaryl groups and aryl groups, including those containing hetero atoms; heterocyclic groups; and oligomeric polyamide groups; preferably the alkyl, alkylaryl, and aryl groups in R have 2 to 12 C atoms and the oligomeric polyamide groups have 1 to 5 polyamide repeat units and most preferably the alkyl, alkylaryl or aryl groups in R have 2 to 8 C atoms and the oligomeric polyamide groups have 1 to 4 polyamide repeat units.

$R_1$ is selected from the group consisting of linear aliphatic or branched aliphatic or cycloaliphatic alkyl groups having at least two C atoms and one alcohol functionality, including those containing heteroatoms, preferably $R_1$ has 2 to 8 C atoms, and most preferably from 2 to 6 C atoms;

$R_2$ is selected from the group consisting of H, linear aliphatic or branched aliphatic or cycloaliphatic alkyl groups and linear aliphatic or branched aliphatic or cycloaliphatic alkyl groups having at least one alcohol functionality, including those containing heteroatoms, preferably the linear or branched alkyl groups in $R_2$ have 1 to 8 C atoms and the linear or branched alkyl groups in $R_2$ that have at least one alcohol functionality have 2 to 8 C atoms and most preferably the linear or branched alkyl groups in $R_2$ have 1 to 6 C atoms and the linear or branched alkyl groups in $R_2$ that have at least one alcohol functionality have 2 to 6 C atoms.

The invention is comprised of the reaction product of "a" moles of at least one polycarboxylic acid R—(COOH)$_n$, where n is greater than or equal to 2, "b" moles of an alkanolamine having either primary or secondary amine functionality, NHR$_1$R$_2$, where R, R$_1$ and R$_2$ are as defined above and b=a×n, and if desired, a quantity of "c" moles of polyamine R—(NHR$_2$)$_m$ where m is at least 2, in which case the quantity of alkanolamine is reduced by the number of moles of amine functionality resulting from the added polyamine [b=(a×n)–(c×m)]. The quantity (c×m) is always less than the quantity (a×n). The amount of polyamine added is preferably such that the total number of moles of primary and secondary amine functionality in the polyamine is from about 0.01 to about 0.9 times the total number of moles of carboxylic acid and most preferably it is from about 0.05 to about 0.78 times the total number of moles of carboxylic acid.

Depending on the reactants the temperature of the reaction can vary greatly. Generally temperatures from about 0° C. to about 250° C. are suitable. When a polycarboxylic acid is used the temperature can be from about 130° C. to 200° C., preferably from about 150° C. to about 180° C.

In their neat form the polyalkanolamides of this invention are amorphous materials (i.e. non-crystalline) that exhibit a distinct glass transition temperature. Differential scanning calorimetry (DSC) was used to assess the glass transition temperature of the neat polyalkanolamides sampled from the reactor after heating was discontinued but before adding water to the reactor. The glass transition temperature of the polyalkanolamides preferably are from −50° C. to +100° C. and most preferably from −40° C. to +80° C. The preferred glass transition temperature of the invention will depend on the intended conditions of use for the polyalkanolamide as well as the identity and properties of other materials used in combination with the polyalkanolamide. The consistency of the neat polyalkanolamides at ambient temperature can range from a syrupy liquid through a gummy solid to a hard solid as the glass transition temperature increases.

The materials of this invention are low molecular weight compounds wherein the oligomeric polyamide groups have number average degrees of polymerization $[DP_n]$ of 1 to 6, preferably 1 to 5, and most preferably 1 to 4. Compounds having number average degrees of polymerization in this range are monomeric $[DP_n=1.0]$ or oligomeric in nature $[1.0<DP_n<6.0]$. In order to prepare compositions with degrees of polymerization higher than 1.0 the Carothers equation is used to calculate the relative ratios of reactants. P. J. Flory, "Principles of Polymer Chemistry", pp. 92–93, Cornell University Press, Ithaca, N.Y. (1953). When the polyacid is a dicarboxylic acid [n=2] and the added polyamine is a diamine [m=2], the degree of polymerization, $DP_n$, can be calculated from Carother's relation: $DP_n=(1+r)/(1-r)$ where $r=a/(b+2c)$ where "b" is always less than "a" and $c=2(a-b)$. For example, in order to obtain a degree of polymerization of 6.0, the diamine needs to be present in a quantity of 0.87 parts per 1.00 parts of diacid, or, b=0.87×a which corresponds to a value of 0.714 for r.

Increasing the molecular weight of the polyalkanolamine can be an effective way to increase the glass transition temperature (Tg). Examples 18 and 23 illustrate the effect of $DP_n$ on Tg. These two polyalkanolamides are comprised of the same starting materials (adipic acid, Dytek A and DEA) but have different proportions of these ingredients to control the $DP_n$. In the case of Example 23 the $DP_n$ is 2.0 and the Tg is −0.7° C. For Example 18 the $DP_n$ is 2.5 and the Tg is 17.2° C. Thus, one can see that relatively minor changes in the $DP_n$ of the polyalkanolamides can have a very strong influence on the glass transition temperature of these materials. Examples 20 and 21 show similar results for polayl-kanolamides made from isophthalic acid, Dytek A and DEA. The Tg of Example 20 with a $DP_n$ of 2.5 is 50.0° C. while the Tg of Example 21 with a $DP_n$ of 2.0 is 45.1° C.

Another way of controlling the glass transition temperature of the polyalkanolamides is to incorporate cyclic structures into the molecule. Some examples would be aromatic polycarboxylic acids, cycloaliphatic polycarboxylic acids, aromatic polyamines, cycloaliphatic polyamines and cyclic alkanolamines. Inclusion of cyclic structures generally tends to increase the glass transition temperature of the resulting material.

The Tg of the polyalkanolamide can have a strong effect on its ability to modify the adhesive properties of a polymer. Controlling the Tg can be important in preparing a polyalkanolamide that will be an effective additive for a particular polymer. The polyalkanolamide Tg can be an important factor in controlling the adhesive behavior of a particular polyalkanolamide/water-soluble polymer blend.

The polycarboxylic acid component of the polyalkanolamide is an organic compound that contains at least 2 carboxylic acid groups. Suitable linear aliphatic polycarboxylic acids are for example malonic acid, glutaric acid, adipic acid, azelaic acid, citric acid, tricarballylic acid (1,2,3-propanetricarboxylic acid), 1,2,3,4-butanetetracarboxylic acid, nitrilotriacetic acid, N,N,N',N'-ethylenediaminetetraacetate. Cyclic aliphatic carboxylic acids may also be used such as 1,2-cyclohexanedicarboxylic acid, 1,3-cyclohexanedicarboxylic acid, 1,4-cyclohexanedicarboxylic acid. Suitable aromatic polycarboxylic acids are, for example, phthalic acid, isophthalic acid, terephthalic acid, 1,2,4-benzenetricarboxylic acid (trimellitic acid) or 1,2,4,5-benzenetetracarboxylic acid (pyromellitic acid).

In an alternate version of the invention acid anhydrides may be used instead of the acid, particularly N,N,N',N'-ethylenediaminetetraacetate dianhydride and the aromatic acid anhydrides phthalic anhydride, mellitic anhydride and pyromellitic anhydride.

Esters of the polycarboxylic acids can also be employed to produce the invention, particularly the methyl or ethyl esters. In this case the alcohol byproduct is distilled off in the synthesis and the synthesis can be performed at a lower temperature than when the carboxylic acid is used. A strongly basic catalyst such as sodium methoxide can be employed in the synthesis of the polyalkanolamides from polycarboxylic esters and alkanolamines. Particular esters of polycarboxylic acids which are suitable include dimethyl adipate, dimethyl malonate, diethyl malonate, dimethyl succinate, and dimethyl glutarate.

Another variation that can be utilized is to react a polycarboxylic acid halide with the alkanolamine. Particularly suitable are the polycarboxylic acid chlorides. In this case the reaction can be performed at very low temperatures. Appropriate polycarboxylic acid halides include adipoyl chloride, glutaryl chloride, and sebacoyl chloride.

Some specific examples of alkanolamines suitable for use in the present invention are: ethanolamine (monoethanolamine, MEA); diethanolamine (DEA); isopropanolamine (monoisopropanolamine); mono-sec-butanolamine; 2-amino-2-methyl-1-propanol; tris (hydroxymethyl)aminomethane; 3-amino-1,2-propanediol; 1-amino-1-deoxy-D-sorbitol; 2-amino-2-ethyl-1,3-propanediol.

Examples of polyamines that can be included to increase molecular weight of the polyalkanolamides are diamines such as ethylenediamine, 1,3-diaminopropane, 1,4-diaminobutane, 1,5-diaminopentane, 1,6-diaminohexane (hexamethylenediamine), Dytek A (2-methyl-1,5-pentanediamine, a product of the DuPont company), 1,2-cyclohexanediamine, 1,3-cyclohexanediamine, 1,4-cyclohexanediamine, 1,3-cyclohexanebis(methylamine) [1,3-bis(aminomethyl)cyclohexane], 1-(2-aminoethyl) piperazine, N-methyl-bis-(aminopropyl) amine (MBAPA, 3,3'-diamino-N-methyldipropylamine), 1,4-bis(2-aminoethyl)piperazine and 1,4-bis(3-aminopropyl) piperazine.

Examples of polyamines that are higher than diamines are tris(2-aminoethyl)amine, N-(2-aminoethyl)-1,3- propanediamine, 3,3'-iminobispropylamine, spermidine, spermine, bis(hexamethylene)triamine or the polyalkylene polyamines such as diethylenetriamine (DETA), triethylenetertamine (TETA) or tetraethylenepentamine (TEPA).

One application of a water-soluble adhesive system is in the production of creped paper. In the case of creping applications, the compositions of the invention can be employed as creping adhesives or as a component of a creping adhesive formulation in accordance with the procedures set forth in Canadian Patent No. 979,579 U.S. Pat. No. 5,338,807, and in U.S. application Ser. No. 08/428,287, filed Apr. 25, 1995, the disclosures of which are incorporated herein by reference.

In this regard, fibrous webs, particularly paper webs, are conventionally subjected to the creping process in order to give them desirable textural characteristics, such as softness and bulk. The creping process typically involves applying creping adhesive—generally in the form of an aqueous solution or dispersion—to a drying surface for the web; preferably, this surface is the surface of a rotating creping cylinder, such as the apparatus known as a Yankee dryer. The web is then adhered to the indicated surface. It is subsequently dislodged from the surface with a creping device—preferably, a doctor blade. The impact of the web against the creping device ruptures some of the fiber-to-fiber bonds within the web, causing the web to wrinkle or pucker. The creping adhesive solution or dispersion can be comprised of one or more adhesive components, typically water-soluble polymers, and may also contain one or more release agent components as well as any other desired additives that may affect the creping process. This is known as the creping adhesive package. A component of this creping package may be the creping release agents disclosed in U.S. application Ser. No. 08/428,287, filed Apr. 25, 1995.

The polyalkanolamide of the present invention can be applied either by itself or in combination with the creping adhesive package to a means for creping a fibrous web, and employing this means to crepe the web. Further in this regard, the creping process of the invention can include the steps of applying the polyalkanolamide either by itself or in combination with the creping adhesive package to a drying surface for the fibrous web, providing a fibrous web, pressing the fibrous web against the drying surface to adhere this web to the surface, and dislodging the fibrous web from the drying surface with a creping device to crepe the fibrous web.

These compositions can be used in their pure form as a creping adhesive composition or may be blended with one or more water-soluble polymers to produce a creping adhesive composition. In addition, the creping adhesive composition can contain release agents, surfactants, salts to adjust the water hardness, acids or bases to adjust the pH of the creping adhesive composition or other useful additives.

The compositions of the present invention have improved the adhesive properties of polyamidoamine-epichlorohydrin resins, polyamine-epichlorohydrin resins and of poly(vinyl alcohol). The polyalkanolamides will also improve the adhesive properties of other synthetic, naturally occurring or synthetically-modified natural water-soluble polymers and copolymers such as polyacrylamide, polymethacrylamide, poly(acrylic acid), poly(methacrylic acid), poly(hydroxyethyl acrylate), poly(hydroxyethyl methacrylate), poly(n-vinyl pyrrolidinone), poly(ethylene oxide), poly(ethylene glycol), hydroxyethyl cellulose (HEC), hydroxypropyl cellulose (HPC), guar gum, starch, agar, alginic acid, and carboxymethyl cellulose (HEC). Other useful water-soluble polymers are the highly branched polyamidoamines disclosed in U.S. application Ser. No. 08/634,266, filed Apr. 18, 1996 or the silyl-linked polyamidoamines disclosed in U.S. application Ser. No. 08/655,965, filed Jun. 19, 1996.

Synthesis of Polyalkanolamides (PAA)

Table 1 lists the conditions for synthesis and some physical properties of a number of polyalkanolamides that have been prepared from polycarboxylic acids and alkanolamines. Table 2. lists several examples of polyalkanolamides made from polycarboxylic acids, alkanolamines and additional specific levels of a polyamine component to increase the molecular weight in a controlled manner. In a typical procedure the alkanolamine(s) and, if desired, polyamine are placed in a resin kettle fitted with a mechanical stirrer, Dean-Stark type water distillation trap and a heating mantle. The polyacid is then added to the kettle while stirring the contents. When the polyacid addition is complete the reaction mixture is heated to 130 to 190° C. and water of condensation is removed through the distillation trap. After 1–4 hours heating is discontinued and a sample of molten resin is removed for analysis. A quantity of water is then added which will yield a solution of polyalkanolamide having approximately 50% solids by weight. Alternately, the polyalkanolamide can be isolated in its neat form by pouring the molten product into a pan to cool. The neat material can be dissolved in water later.

The scope of this invention as claimed is not intended to be limited by the following examples, which are given by way of illustration. All parts are by weight unless otherwise indicated.

EXAMPLE 1

To a 1,000 mL resin kettle fitted with a condenser, Dean-Stark distillation trap, a thermocouple, heating mantle and mechanical paddle-type stainless steel stirrer was added 244.32 g of monoethanolamine (4.0 moles). While stirring the contents of the reactor a quantity of 292.28 g of adipic acid (2.0 mole) was added over a period of 25 minutes. The temperature of the reaction mixture increased to 100° C. due to the exothermic reaction which occurs on combining these two components. The reactor was then heated to 170° C. The temperature was maintained at this value for 3 hours. A total of 59 mL of distillate had been collected at this point (theoretical=72 mL). At this time a sample of the molten material was removed for analysis and the heating was discontinued. A quantity of 430 mL of warm water was then added to the reactor while maintaining stirring in order to dissolve the product. The resulting solution was cooled to ambient temperature and bottled. This product had a total solids content of 51.8% by weight, pH of 8.29, a Brookfield viscosity of 17.5 cPs and had a reduced specific viscosity (RSV) of 0.033 dL/g. Brookfield viscosity was measured at 22° C. using a #2 spindle at 60 rpm and RSV was measured at 25° C. in 1.0M $NH_4Cl$ at a concentration of 2.00 g/dL.

EXAMPLES 2–17

The procedure for synthesizing the polyalkanolamides of Examples 2–17 was similar to that used in Example 1. Conditions of preparation and some properties of the resulting products are listed in Table 1.

EXAMPLE 18

To a 1,000 mL resin kettle fitted with a condenser, Dean-Stark distillation trap, a thermocouple, heating mantle and mechanical paddle-type stainless steel stirrer was added 140.05 g of diethanolamine (1.332 moles) and 95.17 g of 1,2-cyclohexanediamine (mixture of cis and trans, 0.8334 mole). While stirring the contents of the reactor a quantity of 219.21 g of adipic acid (1.50 mole) was added over a period of 20 minutes. The temperature of the reaction mixture increased to 45° C. due to the exothermic reaction which occurs on combining these components. The reactor was then heated to 180° C. The temperature was maintained at this value for 1.83 hours. A total of 54 mL of distillate had been collected at this point (theoretical=54 mL). At this time a sample of the molten material was removed for analysis and the heating was discontinued. A quantity of 400 mL of warm water was then added to the reactor while maintaining stirring in order to dissolve the product. The resulting solution was cooled to ambient temperature and bottled. This product had a total solids content of 49.1% by weight, pH of 6.63, a Brookfield viscosity of 424 cPs and had a reduced specific viscosity (RSV) of 0.052 dL/g. Brookfield viscosity was measured at 22° C. using a #2 spindle at 60 rpm and RSV was measured at 25° C. in 1.0M $NH_4Cl$ at a concentration of 2.00 g/dL.

EXAMPLES 19–25

The procedure for synthesizing the polyalkanolamides of Examples 19–25 was similar to that used in Example 18. Conditions of preparation of and some properties of the resulting products are listed in Table 2. Examples 18 and 19–25 are examples of polyalkanolamides that contained added polyamine to give controlled, higher molecular weights. The reaction of adipic acid, 1,2-diaminocyclohexane and diethanolamine is illustrated in FIG. 10.

Adhesion Testing of Polyalkanolamide Tackifier Formulations

EXAMPLE 26

A device for evaluating the adhesive properties of potential creping adhesives has been constructed. S. P. Dasgupta, Hercules Internal Report, R1 21-135-01, "Development of an Adhesion Measuring Technique: Laboratory Evaluation of Creping Aid Chemicals", Oct. 12, 1992. This apparatus consists of a heated cast iron block that is mounted on the actuator of a MTS® Teststar™ material testing equipment available from the MTS Company, Minneapolis, Minn. This platen is heated to 120° C. A paper sample is attached to the upper platen of the load cell of the test instrument with double sided tape. To perform the test an operator sprays a known quantity of an aqueous solution of creping adhesive with a known concentration onto the heated block. This is accomplished by using an airbrush that has been fitted with a volumetric spray bottle. The volumetric spray bottle allows one to accurately measure the volume of solution that is to be applied to the test platen. Our standard test conditions use a volume of 1.2 mL of a 4.0% solids aqueous solution. The pH of the solution was adjusted to 7.0 prior to testing. After the resin solution is sprayed onto the heated block, the actuator is raised to contact the heated block to the paper sample with a force of 10 kg. The actuator is then lowered and the force to pull the platen away from the paper that it has contacted is measured. This measured force is the adhesion value of the particular resin being tested. Since the applied force is not always exactly 10 kg the adhesion value is normalized to account for slight variations in the applied force. This is accomplished by multiplying the measured adhesion value by [10/(Applied force in kg)]. The paper used for testing is a 40# basis weight sheet prepared from a 50/50 hardwood/softwood bleached Kraft furnish.

Mixtures of the polyalkanolamides of Examples 12 and 13 with Crepetrol® 80E, a PAE creping adhesive commercially available from Hercules Inc., Wilmington Del., were tested for adhesion using the adhesion test described above. All mixtures were calculated on a weight % basis. Results of these tests are listed in Table 3. The adhesion values for the pure polyalkanolamide compositions are also listed. The polyalkanolamides all have much lower adhesion values than Crepetrol® 80E. However, combinations of the two materials show very significant increases in adhesion. A plot of adhesion vs. weight % of polyalkanolamide tackifier resin in the composition are shown in FIG. 2 for the Crepetrol 80E mixtures. The polyalkanolamide tackifying resins have a strong positive effect on the adhesion up to a level of 60% for PAA 12 and shows improved adhesion over the entire range of composition for PAA 13.

EXAMPLE 27

In a similar manner the adhesion of mixtures of the polyalkanolamides of Examples 14, 15 and 16 with Crepetrol® 80E was measured. These results are listed in Table 4. All three polyalkanolamides show significant increases in adhesion up to 50% polyalkanolamide content, the highest level tested. These polyalkanolamides had very low adhesion values when applied in their pure form. These results are plotted in FIG. 3.

EXAMPLE 28

Adhesion was also measured for mixtures of Crepetrol® 80E with two oligomeric polyalkanolamides, prepared with added diamine (Examples 22 and 23). Results of these tests are found in Table 5. Both of these polyalkanolamide tackifiers show excellent increases in adhesion up to a level of 60% polyalkanolamide. Above 60% polyalkanolamide the adhesion drops off. These polyalkanolamides also had low adhesion values when applied in their pure form. The adhesion results of this example are plotted in FIG. 4.

EXAMPLE 29

Adhesion was also measured for a mixture of Crepetrol® 80E with PAA of Example 25, another oligomeric polyalkanolamide prepared with added diamine. Results of these tests are found in Table 6. This particular polyalkanolamide actually showed a decrease in adhesion across the range of composition tested. However, this polyalkanolamide showed the highest adhesion value of all the pure polyalkanolamides (16.7 kg). This is probably due to the high glass transition temperature of this material (72° C.), the highest Tg of all the polyalkanolamides we have prepared. This indicates that the polaylkanolamides should have a relatively low Tg to effectively modify the adhesive properties of Crepetrol® 80E, but that polyalkanolamides with higher Tg values may be useful as adhesives in their pure form. This high Tg polyalkanolamide may also be an effective tackifier resin for a water-soluble polymer having a higher Tg than Crepetrol® 80E. The adhesion results of this example are plotted in FIG. 5.

EXAMPLE 30

The adhesion values for mixtures of polyalkanolamides of Examples 2, 13 and 17 and Kymene® 557 LX, a PAE resin commercially available from Hercules Incorporated, Wilmington Del., are listed in Table 7. Here again, significant increases in adhesion are seen. These results are plotted in FIG. 6. In contrast to the Crepetrol® 80E-polyalkanolamide system, the Kymene® 557 LX-polyalkanolamide blends show a drop in adhesion at a lower level of polyalkanolamide. This level depends on the particular polyalkanolamide used in the formulation.

EXAMPLE 31

The adhesive properties of PAA of Example 2 mixed with Crepetrol® 73, a polyamine-epichlorohydrin resin commercially available from Hercules Incorporated, Wilmington Del., are listed in Table 8. Moderate increases in adhesion are seen at PAA levels up to 15%, at which point the adhesion drops off. These results are plotted in FIG. 7.

EXAMPLE 32

Table 9 lists results of adhesion testing for mixtures of poly(vinyl alcohol) and PAA of Example 2. The poly(vinyl alcohol) used was Airvol 425, a product of Air Products & Chemicals, Inc., Allentown Pa.. The adhesion of this mixture as a function of polyalkanolamide content is plotted in FIG. 8. Although poly(vinyl alcohol) shows much lower adhesion in this test than typical PAE resins, the adhesion is significantly increased by the addition of the tackifying resin of this invention.

EXAMPLE 33

The adhesive properties of another poly(vinyl alcohol)/polyalkanolamide mixture are listed in Table 10. In this case Airvol 540, a product of Air Products & Chemicals, Inc., Allentown Pa., was combined with polyalkanolamide of Example 23. These blends show increasingly higher levels of adhesion, up to a maximum of 22.8 kg at a polyalkanolamide tackifier level of 80%. This is more than double the adhesive value for either pure component. These results are plotted in FIG. 9.

EXAMPLE 34

Table 10 also lists results of the adhesion testing of a 1:1:1 mixture of Crepetrol® 80E, Airvol poly(vinyl alcohol) and polyalkanolamide of Example 23. This mixture exhibited excellent adhesion, which indicates that the polyalkanolamide tackifiers are effective in improving the adhesive properties of a blended poly(vinyl alcohol)/polyamidoamine-epichlorohydrin resin.

TABLE 1

Synthesis of Polyalkanolamides[1]

| Example | Moles Acid[2] | Moles Alkanolamine[3] | Theo. $H_2O$ (mL) | Actual $H_2O$ (mL) | RSV (dL/g) | Solids | B.V. (cPs) | pH | Midpoint $T_g$ (° C.)[4] |
|---|---|---|---|---|---|---|---|---|---|
| 1[5] | 2.0 Adipic | 4.0 MEA | 72 | 59 | 0.0335 | 51.8% | 17.5 | 8.29 | −23.5 |
| 2 | 2.0 Adipic | 2.0 MEA + 2.0 DEA | 72 | 69.5 | 0.0341 | 55.8% | 33.6 | 7.19 | −29.9 |
| 3 | 1.0 Citric | 1.5 MEA + 1.5 DEA | 54 | 71 | 0.0294 | 42.8% | 14.0 | 8.53 | −22.2 |
| 4 | 1.5 Adipic | 1.0 MEA + 1.0 DEA + 1.0 TRIS | 54 | 45 | 0.0336 | 49.8% | 22.0 | 9 01 | −22.5 |
| 5 | 1.5 Glutaric | 1.5 MEA + 1.5 DEA | 54 | 56 | 0.0321 | 48.4% | 18.0 | 7.03 | −27.2 |
| 6 | 1.5 Succinic | 1.5 MEA + 1.5 DEA | 54 | 53 | 0.0311 | 41.1% | 13.0 | 8.11 | −37.0 |
| 7 | 1.5 Adipic | 1.0 MEA + 1.0 DEA + 1.0 AMS | 54 | 36 | 0.0340 | 47.9% | 23.0 | 10.17 | −10.9 |
| 8 | 1.5 Adipic | 3.0 DEA | 54 | 70.5 | 0.0421 | 48.2% | 29.1 | 7.32 | — |
| 9 | 1.5 Succinic | 3.0 MEA | 54 | 44.5 | 0.0344 | 41.3% | — | — | −22.9 |
| 10 | 1.5 Adipic | 3.0 DEA | 54 | 65 | 0.0423 | 48.8% | 30.6 | 7.27 | −22.3 |
| 11 | 1.5 1,3-CYDA | 1.5 MEA + 1.5 DEA | 54 | 57 | 0.0373 | 47.9% | — | — | — |
| 12 | 1.0 BTCA | 2.0 MEA + 2.0 DEA | 72 | 89 | 0.0292 | 46.3% | — | — | −10.1 |
| 13 | 1.5 1,4-CYDA | 1.5 MEA + 1.5 DEA | 54 | 70 | 0.0410 | 48.5% | — | — | 22.5 |
| 14 | 1.0 1,2,4-BTCA | 1.5 ET + 1.5 DET | 54 | 38 | 0.0252 | 48.8% | 22.5 | 6 57 | −11 6 |
| 15 | 1.5 Isophthalic | 1.5 ET + 1.5 DET | 54 | 33 | 0.0249 | 50.1% | 21.0 | 6.02 | −0.1 |
| 16 | 1.0 1,2,4,5-BTDA | 2.0 ET + 2.0 DET | 36 | 20 | 0.0230 | 53.8% | 31.6 | 6.07 | −1.7 |
| 17 | 1.5 Isophthalic | 1.0 ET + 1.0 DET + 1.0 Tris | 54 | 50 | 0.0330 | 57.2% | 60.1 | 6.69 | 30.2 |

[1]. All samples were heated in a resin kettle for 4 hours at 170° C. unless noted otherwise.
[2]. 1,3-CYDA = 1,3-cyclohexanedicarboxylic acid; 1,4-CYDA = 1,4-cyclohexanedicarboxylic acid; BTCA = 1,2,3,4-butanetetracarboxylic acid 1,2,4-BTCA = 1,2,4-benzenetricarboxylic anhydride (mellitic anhydride); 1,2,4,5-BTDA = 1,2,4,5-benzenetetracarboxylic dianhydride (pyromellitic anhydride)
[3]. MEA = monoethanolamine; DEA = Diethanolamine; TRIS = Tris(hydroxymethyl)aminomethane; AMS = 1-Amino-1-deoxy-D-sorbitol
[4]. Glass transition determined by DSC. Heat rate = 20° C./min. Second heat values.
[5]. Sample was heated for 3 hours at 170° C.
[6]. Sample was heated for 3 hours at 170° C. and then 1 hour at 180° C.

TABLE 2

Synthesis of Oligomeric Polyalkanolamides[1]

| Example | Moles Acid | Moles Polyamine | Moles Alkanolamine[2] | Theo. $DP_n$ | Theo. $H_2O$ (mL) | Actual $H_2O$ (mL) | RSV (dL/g) | Solids | B.V. (cPs) | pH | Midpoint $T_g$ (° C.)[3] |
|---|---|---|---|---|---|---|---|---|---|---|---|
| 18 | 1.5 Adipic | 0.8334 DACYHX | 1.332 DEA | 2.50 | 54 | 54 | 0.052 | 49.1% | 424.0 | 6.23 | 17.2 |
| 19[4] | 1.5 IPA | 1.0 DACYHX | 1.0 MEA/1.0 DEA | 1.86 | 54 | 30 | — | 51.2% | 34.1 | 9.31 | 8.8 |
| 20 | 1.5 IPA | 0.833 Dytek A | 1.33 DEA | 2.50 | 54 | 52 | — | — | — | — | 50.0 |
| 21 | 1.5 IPA | 0.5O Dytek A | 2.0 DEA | 2.00 | 54 | 54 | — | 50.8% | 90.2 | 5.13 | 45.1 |
| 22 | 1.5 Adipic | 0.50 Dytek A | 2.0 DEA | 2.00 | 54 | 54 | — | 48.8% | 42.6 | 6.84 | −9 8 |
| 23 | 1.5 Adipic | 0.50 DACYHX | 2.0 DEA | 2.00 | 54 | 61 | — | 50.9% | 44.1 | 6.70 | −0.7 |

TABLE 2-continued

Synthesis of Oligomeric Polyalkanolamides[1]

| Example | Moles Acid | Moles Polyamine | Moles Alkanolamine[2] | Theo. $DP_n$ | Theo. $H_2O$ (mL) | Actual $H_2O$ (mL) | RSV (dL/g) | Solids | B.V. (cPs) | pH | Midpoint $T_g$ (° C.)[3] |
|---|---|---|---|---|---|---|---|---|---|---|---|
| 24 | 1.5 Itaconic | 0.50 DACYHX | 2.0 DEA | 2.00 | 54 | 56 | — | 50.8% | 26.5 | 5.92 | 16.8 |
| 25 | 1.2 1,4-CYDA | 0.4 DACYHX | 1.6 DEA | 2.00 | 43.2 | 37 | — | 51.3% | 109.0 | 6.77 | 72.3 |

[1]. All samples were heated in a resin kettle for 4 hours at 180° C. unless noted otherwise.
[2]. ET = Ethanolamnine; DET = Diethanolamine; TRIS = Tris(hydroxymethyl)aminoethane; AMS = 1-Amino-1-deoxy-D-sorbitol
[3]. Glass transition determined by DSC. Heat rate = 20° C./min. Second heat values.
[4]. Sample was heated for 4 hours at 170° C.

TABLE 3

Example 26: Adhesion Testing of C-80E with PAA 12 and PAA 13

| Adhesive Formulation | Adhesion (kg) |
|---|---|
| 100% C-80E | 19.2 |
| 100% PAA 12 | 8.6 |
| 100% PAA 13 | 11.7 |
| 80% C-80E/20% PAA 12 | 22.4 |
| 60% C-80E/40% PAA 12 | 21.9 |
| 40% C-80E/60% PAA 12 | 20.9 |
| 20% C-80E/80% PAA 12 | 14.1 |
| 80% C-80E/20% PAA 13 | 25.2 |
| 60% C-80E/40% PAA 13 | 25.2 |
| 40% C-80E/60% PAA 13 | 24.7 |
| 20% C-80E/80% PAA 13 | 22.1 |

TABLE 4

Example 27: Adhesion Testing of C-80E with PAA 14, PAA 15 and PAA 16

| % Adhesive | % Tackifier | Adhesion (kg) |
|---|---|---|
| 100% 80E | None | 17.0 |
| 92.5% 80E | 7.5% PAA 14 | 20.1 |
| 85% 80E | 15% PAA 14 | 21.2 |
| 70% 80E | 30% PAA 14 | 22.4 |
| 50% 80E | 50% PAA 14 | 23.8 |
| None | 100% PAA 14 | 6.4 |
| 92.5% 80E | 7.5% PAA 15 | 21.8 |
| 85% 80E | 15% PAA 15 | 23.4 |
| 70% 80E | 30% PAA 15 | 24.5 |
| 50% 80E | 50% PAA 15 | 25.1 |
| None | 100% PAA 15 | 6.4 |
| 92.5% 80E | 7.5% PAA 16 | 22.1 |
| 85% 80E | 15% PAA 16 | 20.8 |
| 70% 80E | 30% PAA 16 | 22.7 |
| 50% 80E | 50% PAA 16 | 24.9 |
| None | 100% PAA 16 | 10.3 |

TABLE 5

Example 28: Adhesion Testing of C-80E with PAA-22 & PAA-23

| Adhesive Formulation | Adhesion (kg) |
|---|---|
| 100% C-80E | 18.8 |
| 80% C-80E/20% PAA 22 | 25.6 |
| 80% C-80E/40% PAA 22 | 27.2 |
| 60% C-80E/60% PAA 22 | 23.7 |
| 20% C-80E/80% PAA 22 | 13.1 |
| 100% PAA 22 | 7.3 |
| 80% C-80E/20% PAA 23 | 27.7 |
| 80% C-80E/40% PAA 23 | 27.1 |
| 60% C-80E/60% PAA 23 | 24.5 |
| 20% C-80E/80% PAA 23 | 15.5 |
| 100% PAA-23 | 9.9 |

TABLE 6

Example 29: Adhesion Testing of C-80E with PAA-25

| Adhesive Formulation | Adhesion (kg) |
|---|---|
| 100% C-80E | 19.1 |
| 80% C-80E/20% PAA 25 | 18.7 |
| 60% C-80E/40% PAA 25 | 14.0 |
| 40% C-80E/60% PAA 25 | 13.4 |
| 20% C-80E/80% PAA 25 | 14.0 |
| 100% PAA 25 | 16.7 |

TABLE 7

Example 30: Adhesion Testing of Kymene ® 557LX with PAA 2, PAA 13 and PAA 17

| % Adhesive | % Modifier | Adhesion (kg) |
|---|---|---|
| 100% 557LX | None | 18.3 |
| 92.5% 557LX | 7.5% PAA 2 | 19.5 |
| 85% 557LX | 15% PAA 2 | 20.5 |
| 70% 557LX | 30% PAA 2 | 22.6 |
| 50% 557LX | 50% PAA 2 | 18.1 |
| 92.5% 557LX | 7.5% PAA 17 | 22.4 |
| 85% 557LX | 15% PAA 17 | 25.1 |
| 70% 557LX | 30% PAA 17 | 25.2 |
| 50% 557LX | 50% PAA 17 | 23.8 |
| 92.5% 557LX | 7.5% PAA 13 | 24.7 |
| 85% 557LX | 15% PAA 13 | 23.1 |
| 70% 557LX | 30% PAA 13 | 22.9 |
| 50% 557LX | 50% PAA 13 | 22.4 |

TABLE 8

Example 31: Adhesion Testing of Crepetrol ® 73 with PAA 2

| % Adhesive | % Tackifier | Adhesion (kg) |
|---|---|---|
| 100% C-73 | 0% | 20.7 |
| 92.5% C-73 | 7.5% PAA 2 | 22.2 |

TABLE 8-continued

Example 31: Adhesion Testing of Crepetrol ® 73 with PAA 2

| % Adhesive | % Tackifier | Adhesion (kg) |
|---|---|---|
| 85% C-73 | 15% PAA 2 | 22.6 |
| 70% C-73 | 30% PAA 2 | 16.5 |

TABLE 9

Example 32: Adhesion Testing of Airvol 425 with PAA 2

| % Adhesive | % Modifier | Adhesion (kg) |
|---|---|---|
| 100% Airvol 425 | None | 4.1 |
| 92.5% Airvol 425 | 7.5% PAA 2 | 5.0 |
| 85% Airvol 425 | 15% PAA 2 | 6.3 |
| 70% Airvol 425 | 30% PAA 2 | 6.9 |
| 50% Airvol 425 | 50% PAA 2 | 6.9 |

TABLE 10

Example 33: Adhesion Testing of Airvol 540 with PAA 23

| Adhesive Formulation | Adhesion (kg) |
|---|---|
| 100% Airvol 540 sol'n. | 5.98 |
| 20% D-932/80% Airvol 540 sol'n | 11.3 |
| 40% D-932/60% Airvol 540 sol'n | 15.1 |
| 60% D-932/40% Airvol 540 sol'n | 20.4 |
| 80% D-932/20% Airvol 540 sol'n | 22.8 |
| 100% PAA-23 | 10.8 |
| 100% C-80E | 19.9 |
| 33% C-80E/33% Airvol 540/33% PAA 23 | 26.5 |

What is claimed is:

1. A water soluble polyalkanolamide having the formula:

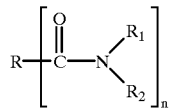

wherein n is an integer from 2 to 10,

R is selected from the group consisting of linear aliphatic or branched aliphatic or cycloaliphatic alkyl groups, alkylaryl groups, and aryl groups, including those containing hetero atoms; heterocyclic groups; and oligomeric polyamide groups having a degree of polymerization ($DP_n$) of from about 1 to 6;

$R_1$ is selected from the group consisting of linear aliphatic or branched aliphatic or cycloaliphatic alkyl groups having at least two C atoms and one alcohol functionality, including those containing heteroatoms;

$R_2$ is selected from the group consisting of H, linear aliphatic or branched aliphatic or cycloaliphatic alkyl groups and linear aliphatic or branched aliphatic or cycloaliphatic alkyl groups having at least one alcohol functionality, including those containing heteroatoms.

2. The polyalkanolamide of claim 1 wherein n is an integer from 2 to 6.

3. The polyalkanolamide of claim 1 wherein the alkyl, alkylaryl, or aryl groups in R have 2 to 12 C atoms and the oligomeric polyamide groups have 1 to 5 polyamide repeat units.

4. The polyalkanolamide of claim 1 wherein $R_1$ has 2 to 8 C atoms.

5. The polyalkanolamide of claim 1 wherein $R_2$ is selected from the group consisting of H, linear aliphatic or branched aliphatic alkyl groups having 1 to 8 C atoms, and linear aliphatic or branched aliphatic or cycloaliphatic alkyl groups having 2 to 8 C atoms and at least one alcohol functionality.

6. The polyalkanolamide of claim 1 containing oligomeric polyamide group derived from a polyamine selected from the group consisting of ethylenediamine, 1,3-diaminopropane, 1,4-diaminobutane, 1,5-diaminopentane, 1,6-diaminohexane, 2-methyl-1,5-pentanediamine, 1,2-cyclohexanediamine, 1,3-cyclohexanediamine, 1,4-cyclohexanediamine, 1,3-cyclohexanebis(methylamine), 1-(2-aminoethyl)piperazine, N-methyl-bis-(aminopropyl)amine, 1,4-bis(2-aminoethyl)piperazine, 1,4-bis(3-aminopropyl)piperazine, tris(2-aminoethyl)amine, N-(2-aminoethyl)-1,3-propanediamine, 3,3'-iminobispropylamine, spermidine, spermine, bis(hexamethylene)triamine, diethylenetriamine, triethylenetertamine or tetraethylenepentamine.

7. The polyalkanolamide of claim 1 containing oligomeric polyamide group derived from a polyamine wherein the total number of moles of primary and secondary amine functionality in the polyamine is from about 0.01 to 0.9 times the total number of moles of carboxylic acid and the polyamine is selected from the group consisting of 1,6-diaminohexane, 2-methyl-1,5-pentanediamine, 1,2-cyclohexanediamine, 1,4-cyclohexanediamine, 1-(2-aminoethyl)piperazine, tris(2-aminoethyl)amine, bis(hexa-methylene)triamine and diethylenetriamine.

8. The polyalkanolamide of claim 1 having a glass transition temperature (Tg) of from about $-50°$ C. to about $+100°$ C.

9. The polyalkanolamide of claim 2 having a glass transition temperature (Tg) of from about $-50°$ C. to about $+100°$ C. containing oligomeric polyamide group derived from a polyamine wherein the total number of moles of primary and secondary amine functionality in the polyamine is from about 0.01 to about 0.9 times the total number of moles of carboxylic acid and the polyamine is selected from the group consisting of 1,6-diaminohexane, 2-methyl-1,5-pentanediamine, 1,2-cyclohexanediamine and diethylenetriamine and wherein "n" is an integer from 2 to 6, the alkyl, alkylaryl, or aryl groups in R have 2 to 12 C atoms and the oligomeric polyamide groups have 1 to 5 polyamide repeat units, $R_1$ has 2 to 8 C atoms, and $R_2$ is selected from the group consisting of H linear aliphatic or branched aliphatic or cycloaliphatic alkyl groups having 1 to 8 C atoms and linear aliphatic or branched aliphatic or cycloaliphatic alkyl groups having 2 to 8 C atoms and at least one alcohol functionality.

10. The polyalkanolamide of claim 9 wherein the oligomeric polyamide group in R has a $DP_n$ of from about 1 to about 4.

11. The polyalkanolamide of claim 9 wherein n is an integer from 2 to 4.

12. The polyalkanolamide of claim 9 wherein the alkyl, alkylaryl or aryl groups in R have 2 to 8 C atoms and the oligomeric polyamide groups have 1 to 4 polyamide repeat units.

13. The polyalkanolamide of claim 9 wherein $R_1$ has 2 to 6 C atoms.

14. The polyalkanolamide of claim 9 wherein $R_2$ is selected from the group consisting of H, linear aliphatic or branched aliphatic or cycloaliphatic alkyl groups having 1 to 6 C atoms and linear aliphatic or branched aliphatic or cycloaliphatic alkyl groups having 2 to 6 atoms and at least one alcohol functionality.

15. The polyalkanolamide of claim 9 containing oligomeric polyamide group derived from a polyamine wherein the total number of moles of primary and secondary amine functionality in the polyamine is from about 0.05 to about 0.78 times the total number of moles of carboxylic acid and the polyamine is selected from the group consisting of 1,6-diaminohexane, 2-methyl-1,5-pentanediamine, 1,2-cyclohexanediamine and diethylenetriamine.

16. The polyalkanolamide of claim 9 having a glass transition temperature of from about −40° C. to about +80° C.

17. The polyalkanolamide of claim 10 having a glass transition temperature of from about −40° C. to about +80° C. containing a polyamine wherein the total number of moles of primary and secondary amine functionality in the polyamine is from about 0.05 to about 0.78 times the total number of moles of carboxylic acid and the polyamine is selected from the group, consisting of 1,6-diaminohexane, 2-methyl-1,5-pentanediamine, 1,2-cyclohexanediamine and diethylenetriamine, and wherein: n is an integer from 2 to 4, the alkyl, alkylaryl or aryl groups in R have 2 to 8 C atoms and the oligomeric polyamide groups have 1 to 4 polyamide repeat units, $R_1$ has 2 to 6 C atoms, $R_2$ is selected from the group consisting of H, linear aliphatic or branched aliphatic or cycloaliphatic alkyl groups having 1 to 6 C atoms and linear aliphatic or branched aliphatic or cycloaliphatic alkyl groups having 2 to 6 atoms and at least one alcohol functionality.

18. The polyalkanolamide of claim 1 wherein R is the alkyl, alkylaryl, aryl or heterocyclic group remaining after the carboxylic groups are removed from malonic acid, glutaric acid, adipic acid, azelaic acid, citric acid, 1,2,3-propanetricarboxylic acid, 1,2,3,4-butanetetracarboxylic acid, nitrilotriacetic acid, N,N,N',N'-ethylenediaminetetraacetate, 1,2-cyclohexanedicarboxylic acid, 1,3-cyclohexanedicarboxylic acid, 1,4-cyclohexanedicarboxylic acid, phthalic acid, isophthalic acid, terephthalic acid, 1,2,4-benzenetricarboxylic acid and 1,2,4,5-benzenetetracarboxylic acid.

19. The polyalkanolamide of claim 9 wherein R is the alkyl, aryl or heterocyclic group remaining after the carboxylic groups are removed from malonic acid, glutaric acid, adipic acid, azelaic acid, citric acid, 1,2,3-propanetricarboxylic acid, 1,2,3,4-butanetetracarboxylic acid, nitrilotriacetic acid, N,N,N',N'-ethylenediaminetetraacetate, 1,2-cyclohexanedicarboxylic acid, 1,3-cyclohexanedicarboxylic acid and 1,4-cyclohexanedicarboxylic acid.

20. The polyalkanolamide of claim 9 wherein $R_1$ is the alkyl group remaining after the amino group has been removed from monoethanolamine, diethanolamine, monoisopropanolamine, mono-sec-butanolamine, 2-amino-2-methyl-1-propanol, tris(hydroxymethyl)aminomethane, 3-amino-1,2-propanediol, 1-amino-1-deoxy-D-sorbitol and 2-amino-2 ethyl-1,3-propanediol.

21. The polyalkanolamide of claim 9 wherein $R_2$ is H, or the alkyl group remaining after the amino group has been removed from monoethanolamine, diethanolamine, monoisopropanolamine, mono-sec-butanolamine, 2-amino-2-methyl-1-propanol, tris(hydroxymethyl) aminomethane, 3-amino-1,2-propanediol, 1-amino-1-deoxy-D-sorbitol and 2-amino-2 ethyl-1,3-propanediol.

22. The polyalkanolamide of claim 17 wherein R is the alkyl group remaining after the carboxylic groups are removed from adipic acid, 1,2,3,4-butanetetracarboxylic acid, 1,3-cyclohexanedicarboxylic acid and 1.4-cyclohexanedicarboxylic acid.

23. The polyalkanolamide of claim 17 wherein $R_1$ is the alkyl group remaining after the amino group has been removed from monoethanolamine, diethanolamine, isopropanolamine and tris(hydroxymethyl)aminoethane.

24. The polyalkanolamide of claim 17 wherein $R_2$ is H, or the alkyl group remaining after the amino group has been removed from monoethanolamine, diethanolamine isopropanolamine and tris(hydroxymethyl)aminoethane.

25. A process to prepare water soluble polyalkanolamides comprising:
(i) reacting "a" moles of at least one polycarboxylic acid, or its anhydride, ester or halide derivative, wherein the polycarboxylic acid has the formula R—(—COOH)$_n$ where n is an integer from 2 to 10,
R is selected from the group consisting of linear aliphatic or branched aliphatic or cycloaliphatic alkyl groups, alkylaryl groups, and aryl groups, including those containing hetero atoms; and heterocyclic groups;
with "b" moles of at least one alkanolamine having the formula NHR$_1$ R$_2$, wherein b=a×n,
$R_1$ is selected from the group consisting of linear aliphatic or branched aliphatic or cycloaliphatic alkyl groups having at least two C atoms and one alcohol functionality, including those containing heteroatoms;
$R_2$ is selected from the group consisting of H, linear aliphatic or branched aliphatic or cycloaliphatic alkyl groups and linear aliphatic or branched aliphatic or cycloaliphatic alkyl groups having at least one alcohol functionality, including those containing heteroatoms;
and optionally with "c" moles of a polyamine having the formula R—(—NHR$_2$)$_m$, where m is an integer and is at least 2, and R and $R_2$ are as above, provided that when a polyamine is present b=(a×n)−(c×m) and (c×m)<(a×n) and
(ii) removing the condensation by product water, alcohol or hydrogen halide.

26. The process of claim 25 wherein the reaction is carried out at a temperature of from about 0° C. to about 250° C.

27. The process of claim 25 wherein a polycarboxylic acid is reacted with the alkanolamine and optionally with the polyamine and wherein n is an integer from 2 to 6 and the alkyl, alkylaryl, or aryl groups in R have 2 to 12 C atoms.

28. The polyalkanolamide of claim 25 wherein $R_1$ has 2 to 8 C atoms, and $R_2$ is selected from the group consisting of H, linear aliphatic or branched aliphatic or cycloaliphatic alkyl groups having 1 to 8 C atoms, and linear aliphatic or branched aliphatic or cycloaliphatic alkyl groups having 2 to 8 C atoms and at least one alcohol functionality.

29. The polyalkanolamide of claim 25 wherein a polycarboxylic acid is employed and the reaction is carried out at a temperature of from about 130° C. to about 200° C.

30. The process of claim 27 wherein $R_1$ has 2 to 8 C atoms, $R_2$ is selected from the group consisting of H, linear aliphatic or branched aliphatic or cycloaliphatic alkyl groups having 1 to 8 C atoms, and linear aliphatic or branched aliphatic or cycloaliphatic alkyl groups having 2 to 8 C atoms and at least one alcohol functionality and wherein a polycarboxylic acid is employed and the reaction is carried out at a temperature of from about 130° C. to about 200° C.

31. The process of claim 30 wherein n is an integer from 2 to 4, and the alkyl, alkylaryl or aryl groups in R have 2 to 8 C atoms.

32. The process of claim 30 wherein $R_1$ has 2 to 6 C atoms, and $R_2$ is selected from the group consisting of H, linear aliphatic or branched aliphatic or cycloaliphatic alkyl groups having 1 to 6 atoms and linear aliphatic or branched aliphatic or cycloaliphatic alkyl groups having 2 to 6 atoms and at least one alcohol functionality.

33. The process of claim 30 employing a polyamine in an amount such that the total number of moles of primary and secondary amine functionality in the polyamine is from about 0.05 to about 0.78 times the total number of moles of carboxylic acid and the polyamine is selected from the group consisting of 1,6-diaminohexane, 2-methyl-1,5-pentanediamine, 1,2-cyclohexanediamine and diethylenetriamine.

34. The process of claim 30 wherein a polycarboxylic acid is employed and the reaction is carried out at a temperature of from about 150° C. to about 180° C.

35. The process of claim 31 wherein $R_1$ has 2 to 6 C atoms, and $R_2$ is H, a linear or branched alkyl group having 1 to 6 C atoms, and $R_2$ is selected from the group consisting of H, linear aliphatic or branched aliphatic or cycloaliphatic alkyl groups having 1 to 6 C atoms, and linear aliphatic or branched aliphatic or cycloaliphatic alkyl groups having 2 to 6 C atoms and at least one alcohol functionality; employing a polyamine in an amount such that the total number of primary and secondary amine functionality in the polyamine is from about 0.05 to about 0.78 and the polyamine is selected from the group consisting of 1,6-diamino-hexane, 2-methyl-1,5-pentanediamine, 1,2-cyclohexanediamine and diethylenetriamine and the reaction is carried out at a temperature of from about 150° C. to about 180° C.

36. The process of claim 30 wherein the polycarboxylic acid is selected from the group consisting of malonic acid, glutaric acid, adipic acid, azelaic acid, citric acid, 1,2,3-propanetricarboxylic acid, 1,2,3,4-butanetetracarboxylic acid, nitrilotriacetic acid, N,N,N',N'-ethylenediaminetetraacetate, 1,2-cyclohexanedicarboxylic acid, 1,3-cyclohexanedicarboxylic acid, 1,4-cyclohexanedicarboxylic acid, phthalic acid, isophthalic acid, terephthalic acid, 1,2,4-benzenetricarboxylic acid and 1,2,4,5-benzenetetracarboxylic acid.

37. The process of claim 30 wherein the alkanolamine is selected from the group consisting of monoethanolamine, diethanolamine, monoisopropanolamine, mono-sec-butanolamine, 2-amino-2-methyl-1-propanol, tris(hydroxymethyl)aminomethane, 3-amino-1,2-propanediol, 1-amino-1-deoxy-D-sorbitol and 2-amino-2 ethyl-1,3-propanediol.

38. A composition comprising (a) the polyalkanolamide of claim 1 and (b) at least one synthetic, natural or synthetically modified natural water soluble polymer or copolymer.

39. A composition comprising (a) the polyalkanolamide of claims 1 and (b) at least one synthetic, natural or synthetically modified natural water soluble polymer or copolymer, selected from the group consisting of polyamidoamine-epichlorohydrin resins, polyamine-epichlorohydrin resins, poly(vinyl alcohol), polyacrylamide, polymethacrylamide, poly(acrylic acid), poly(methacrylic acid), poly(hydroxyethyl acrylate), poly(hydroxyethyl methacrylate), poly(N-vinyl pyrrolidinone), poly(ethylene oxide), poly (ethylene glycol), hydroxyethyl cellulose, hydroxypropyl cellulose, guar gum, starch, agar, alginic acid, carboxymethyl cellulose, highly branched polyamidoamines, and silyl-linked polyamidoamines.

40. A composition comprising (a) the polyalkanolamide of claim 1 and (b) at least one synthetic, natural or synthetically modified natural water soluble polymer or copolymer selected from the group consisting of polyamidoamine-epichlorohydrin resins, polyamine-epichlorohydrin resins, poly(vinyl alcohol), highly branched polyamidoamines, and silyl-linked polyamidoamines, polyacrylamide, poly (ethylene oxide), poly (ethylene glycol), hydroxyethyl cellulose, hydroxypropyl cellulose, carboxymethyl cellulose and guar gum.

41. A composition comprising (a) the polyalkanolamide of claim 1 and (b) at least one synthetic, natural or synthetically modified natural water soluble polymer or copolymer selected from the group consisting of polyamidoamine-epichlorohydrin resins, polyamine-epichlorohydrin resins, poly(vinyl alcohol), highly branched polyamidoamines, and silyl-linked polyamidoamines.

* * * * *